Aug. 6, 1957 R. S. MOORE Plant Pat. 1,631
ROSE PLANT
Filed Oct. 16, 1956
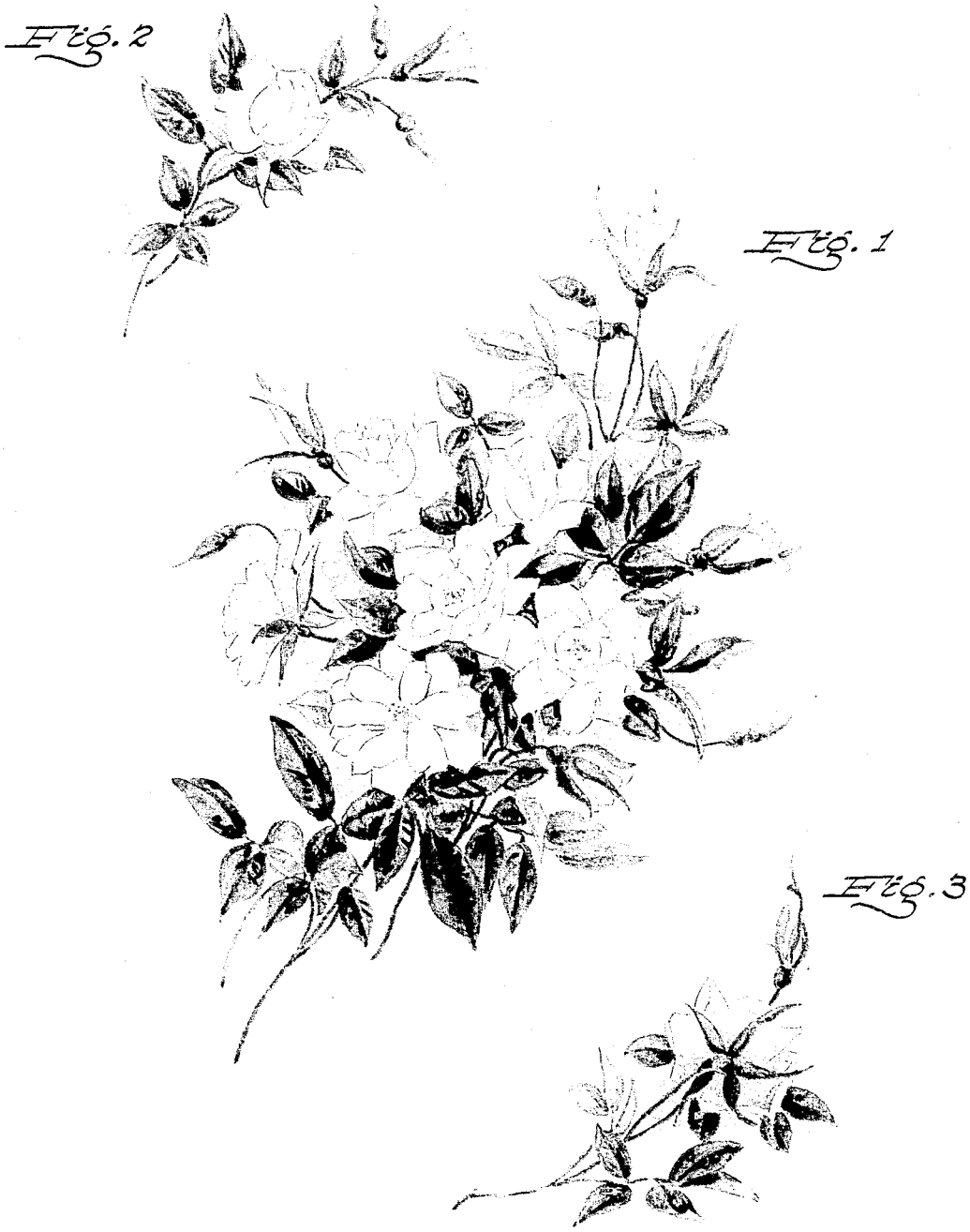
WITNESS
Addison J. Avery
INVENTOR
Ralph S. Moore
Webster & Webster
ATTYS.

United States Patent Office

Plant Pat. 1,631
Patented Aug. 6, 1957

1,631

ROSE PLANT

Ralph S. Moore, Visalia, Calif.

Application October 16, 1956, Serial No. 616,359

1 Claim. (Cl. 47—61)

This invention relates to a new and distinct variety of bush-type rose plant, of the miniature class, which bears dainty flowers of bright and clear, or buttercup, yellow color.

The variety was originated by me in my nursery in Visalia, Tulare County, California, as a seedling resulting from a cross of Copper Glow as the seed parent, and an unnamed seedling (Carolyn Dean × Tom Thumb) as the pollen parent. The Copper Glow and Tom Thumb varieties are the subject of United States Plant Patents Nos. 458 and 169, respectively, whereas said unnamed seedling and the Carolyn Dean varieties are unpatented.

Subsequent to its origination, and the recognition that the variety had distinctive characteristics which made it desirable for commercial nursery growing, such variety was successfully asexually reproduced by me in my nursery, located as aforesaid, both by cuttings and budding; all of the asexual reproductions having been found to carry forward the characteristics of the original plant.

The present variety of miniature rose plant—in comparison to the Baby Gold Star (United States Plant Patent No. 407)—can be generally distinguished, as to novelty, by being a faster, easier, and more economical plant to propagate and grow; by a better bud; and by a brighter yellow color of the flowers.

More particularly—and with respect to the rooting and growth characteristics—the present variety roots faster, with a much higher percentage of successful rootings from cuttings, and with many fine roots that are not easily broken and which thus materially facilitates handling and potting; the variety growing easier and faster to salable size, as well as more uniformly.

Further—and with respect to the plant and its foilage—there is a more spreading and branching habit, with smaller foilage, but in greater abundance.

Additionally—and with respect to the flowers—they are a light or generally buttercup yellow rather than a gold yellow; a larger amount of flowers being borne on the plant, and there being more continuity of bloom.

In the drawings:

Fig. 1 shows a spray, including foilage, buds, and flowers.

Fig. 2 is a front elevation of a single stem with a flower and buds.

Fig. 3 is a rear elevation of the same.

Referring now specifically to the new and distinct variety of rose plant, the following is a detailed description thereof in outline; all major color plate identification being by Maerz and Paul Dictionary of Color.

Type: Bush; dwarf; hardy; greenhouse; outdoors; pot plant; cut flowers; garden decoration.

Class: Miniature.

Flowers:

*Continuity.*—Continuous.

*Fragrance.*—Moderate; tea rose.

Flowers Borne: Singly—two to five on strong, medium length stem.

Quantity of bloom: Abundant, both outdoors and in greenhouse.

Bud:

*Peduncle.*—Medium length; medium thickness; erect; stiff; yellowish green; numerous green hairs.

*Before calyx breaks.*—Size—small. Form—long; pointed, with slender foliaceous parts extending beyond the tip of the bud equal to one-quarter or more of its length. Color—green (22–L–8).

*As calyx breaks.*—Color—yellow (9–L–3), sometimes splashed with a bit of red.

*As first petal opens.*—Size—very small. Form—long; pointed. Color—yellow (9–L–3 to 9–L–6). Opening—opens well at all times.

Bloom:

*Size when fully open.*—Very small, average 1¼" to 1½".

*Petalage.*—Double, with from 18 to 20 petals arranged irregularly. Occasionally up to 30 to 40 narrow petals.

*Form.*—Open; cupped. Petals remain at first loosely rolled outward, later becoming very loosely rolled outward.

Petals: Medium thick, with both inside and outside satiny.

*Shape.*—Outside — obovate. Intermediate—lanceolate. Inside — lanceolate, linear.

*Color.*—A bright and clear, or buttercup yellow (9–L–3 to 9–L–6), shading at the extremities to a still lighter yellow (9–K–1). On flowers open several days the color tends to soften to a primrose yellow similar to the Mermaid variety, which is a single-flowered climber (unpatented).

*Behavior.*—Old flowers persist.

*Flower longevity.*—Bush in garden—average 2 to 4 days in summer months. Cut flowers indoors—average 2 days.

*Reproductive organs*

Stamens: Medium number; arranged irregularly; mixed with petaloids.

Filaments: Medium length; yellow; most with anthers.

Anthers: Very small; yellowish brown; open at various times.

Pollen: Sparse; yellow.

Pistils: Medium number.

Styles: Even; medium length; very thin; loosely bunched.

Stigma: Yellow.

Ovaries: All enclosed.

Hips: None observed.

Sepals: Permanent; long; straight; spear shaped; light green.

Seeds: None.

*Plant*

Foilage:

*Leaves.*—Compound of five leaflets; abundant; moderately soft and semi-glossy. Color: top side—medium green (22–L–8); under side—lighter grey green (21–J–6); very young leaves sometimes tinted light red or bronze.

*Leaflets.*—Lanceolate, with apex acute. Base—acute. Margin—serrate.

*Rachis.*—Light. Upper side—grooved. Under side—sparsely hairy, thorny.

*Stipules.*—Medium length. Moderately narrow, with medium length points turning out at an angle of more than 45 degrees.

Growth:

*Habit.*—Dwarf; bushy; much branched.

*Growth.*—Vigorous.

*Canes.*—Medium.

*Main stems.*—Color—green. Thorns—several; medium length; hooked downward, with short narrow base. Prickles—few; greyish brown. Hairs—few; greyish brown.

*Branches.*—Color—green. Thorns—several; medium length; hooked downward, with short narrow base. Prickles—few; green. Hairs—few; green.

*New shoots.*—Color—green. Thorns—several; medium length; hooked downward, with short narrow base. Prickles—none to few. Hairs—none.

The miniature rose plant and its flowers as herein described may vary in slight detail due to climatic and soil conditions under which the variety may be grown.

The following is claimed:

A new and distinct variety of ever-blooming, bush-type, miniature rose plant, substantially as described and illustrated, characterized—in comparison to the Baby Gold Star—by faster rooting, with many fine roots, and a higher percentage of successful rootings from cuttings; by growing more vigorously and uniformly; by a more spreading and branching habit, with smaller foliage, but in greater abundance; and by bright and clear yellow flowers borne in greater profusion on the plant, and with more continuity of bloom.

No references cited.